United States Patent [19]
Pang et al.

[11] Patent Number: 5,882,649
[45] Date of Patent: *Mar. 16, 1999

[54] ORAL VACCINE COMPRISING ANTIGEN SURFACE-ASSOCIATED WITH RED BLOOD CELLS

[75] Inventors: Gerald Toh Pang; Robert Llewellyn Clancy, both of New South Wales; Allan William Cripps, Curtin; Margaret Lorraine Dunkley, New South Wales, all of Australia

[73] Assignee: Flustat Pty. Ltd., Australia

[*] Notice: The term of this patent shall not extend beyond the expiration date of Pat. No. 5,643,577.

[21] Appl. No.: 778,605

[22] Filed: Jan. 6, 1997

Related U.S. Application Data

[63] Continuation-in-part of Ser. No. 940,899, Oct. 23, 1992, Pat. No. 5,643,577.

[30] Foreign Application Priority Data

Apr. 24, 1990 [AU] Australia .................. PJ 9783/90

[51] Int. Cl.⁶ .................. A61K 39/12; A61K 39/385; C07K 1/00; C07K 14/00
[52] U.S. Cl. .................. 424/206; 424/196.11; 424/194.1; 424/193.1; 424/204.1; 530/350
[58] Field of Search .................. 424/196.11, 206, 424/194.1, 193.1, 204.1; 530/350

[56] References Cited

U.S. PATENT DOCUMENTS

| | | | |
|---|---|---|---|
| 4,157,390 | 6/1979 | Parry et al. | 424/92 |
| 4,403,037 | 9/1983 | Coates | 436/521 |
| 4,904,468 | 2/1990 | Gill et al. | 424/89 |
| 5,075,109 | 12/1991 | Tice et al. | 424/88 |
| 5,643,577 | 7/1997 | Pang et al. | 424/206.1 |

FOREIGN PATENT DOCUMENTS

| | | |
|---|---|---|
| 1563839 | 4/1980 | United Kingdom. |
| 1580539 | 12/1980 | United Kingdom. |

OTHER PUBLICATIONS

Chaicumpa, et al. "Oral Vaccine Against Choler . . . " Southeast Asian J. Trop Med Pub Health 18(2):142–148 (Abstract), 1987.

Colwell, et al. (1986) "Method for Generating a High Frequency of Hybridomas Producing Monoclonal IgA Antibodies", *Methods of Enzymology* 121: 42–51.

Farag–Mahmod, et al. (Jun. 1988) "Immunogenicity and Efficacy of Orally Administered Inactivated Influenza Virus Vaccine in Mice", *Vaccine* 6:262–268.

Jones, et al. (1988) "Cellular Immune Responses in the Murine Lung to Local Immunization with Influenza A Virus Glycoproteins in Micelles and Immunostimulatory Complexes (Iscoms)", *Scand. J. Immunol.* 27:645–652.

Kreuter, et al. (Apr. 1981) "Long–Term Studies of Microencapsulated and Adsorbed Influenza Vaccine Nanoparticles", *Journal of Pharmaceutical Sciences* 70(4):367–371.

Milch, et al. (1988) *PNAS* 85(5):1610–1614, Abstract.

Mullenhacker, et al. (1988) *Immunol. Cell Biol.* 66:153–157.

Pang, et al. (Feb. 1992) "A Novel Particulate Influenza Vaccine Induces Long–Term and Broad–Based Immunity in Mice after Oral Immunization", *Journal of Virology*:1162–1170.

Posnett, et al. (1988) "A Novel Method for Producing Anti–Peptide Antibodies", *J. Biol. Chem.* 263(4):1719–1725.

(List continued on next page.)

*Primary Examiner*—Lynette F. Smith
*Attorney, Agent, or Firm*—Scully, Scott, Murphy & Presser

[57] ABSTRACT

Red blood cells or derivatives thereof such as ghost preparations, whole cell membrane preparations or fragments thereof, can act as a potent carrier for orally administered antigens. Mucosal immunity in particular can be effectively induced against such viruses as influenza when adsorbed to chicken red blood cells and orally administered.

21 Claims, 14 Drawing Sheets

OTHER PUBLICATIONS

Waugh, et al. (1976) "Viscoelastic Properties of Erythrocyte Membranes of Different Vertebrate Animals", *Microvasc. Res.* 12:291–304, Abstract.

White, et al. (1986) *Medical Virology*, Academic Press, New York, pp. 509–512.

Derwent Abstract Accession No. 83738B/46, SU,A 649435 (UFA Vaccine Sera), Feb. 28, 1979.

Derwent Abstract Accession No. 55028A/30, SU,A 562064 (Sverd Virus Infect), Oct. 10, 1977.

Derwent Abstract Accession No. 85–089709/15, Class J04, JP,A 60–038645 (Green Cross Corp.), Feb. 28, 1985.

FIG. 7

PFU PER ML (Log 10)

CONTROL    H3N2 H1N1 H2N2
           IMMUNISED
SURFACE ANTIGENS

ORAL VACCINE COMPRISING ANTIGEN SURFACE-ASSOCIATED WITH RED BLOOD CELLS

CROSS-REFERENCE TO RELATED APPLICATIONS

The present application is a continuation-in-part of U.S. patent application Ser. No. 07/940,899, filed 23 Oct. 1992, now U.S. Pat. No. 5,643,577 (based on International Application No. PCT/AU91/00519, WO 91/16073, dated 24 Apr. 1991), the disclosure of which is incorporated herein by reference.

FIELD OF THE INVENTION

This invention relates generally to vaccines, and in particular to vaccines appropriate for oral administration.

BACKGROUND OF THE INVENTION

Currently, most vaccines are administered parenterally with consequent problems arising from the invasive nature of the administration route. For instance, it has been proposed, in U.S. Pat. No. 4,157,390, to use red blood cells as vehicles for the presentation of enteropathogenic antigens in a parenteral vaccine administered to prepartum sows. A disadvantage of parenteral administration is that, in general, it induces a better blood borne immune response than a mucosal one, yet the prophylaxis or treatment of some infective agents is more appropriately dealt with by a strong mucosal immunity. The parenteral nature of prior art vaccines has not in general resulted in a strong mucosal response.

To redress some of these problems, orally administered vaccines have been proposed against various infective agents. Unfortunately as the alimentary tract provides a hostile environment, it is only fortuitously, such as in the Sabin vaccine, that these have been effective.

It is an object of the present invention to provide a vaccine, appropriate for oral administration, which redresses some of the disadvantages experienced in the past.

SUMMARY OF THE INVENTION

It has now been found that red blood cells and their derivatives such as ghost or whole membrane preparations and fragments thereof, can provide a potent orally administered vehicle for the presentation of antigens to the mucosal immune system.

In accordance with a first aspect of the invention, there is provided an oral vaccine comprising an antigen derived from an agent which infects the mucosa in mammals, wherein said antigen is surface-associated with a red blood cell, a ghost preparation thereof, or a whole cell membrane preparation or fragments thereof, and wherein said vaccine elicits a mucosal immune response in mammals.

A second aspect of the invention provides a method of eliciting a mucosal immune response in a mammal, the method comprising the oral administration to said mammal of a vaccine as described above in an amount effective to elicit said mucosal immune response.

Preferably, the mammal is a human.

DETAILED DESCRIPTION OF THE INVENTION

In general, the antigen will derive from any etiological agent which infects the mucosa, in particular one which infects at least one of the respiratory tract or alimentary tract of a mammal. Such an infectious agent may be a virus, in particular those viruses in which a mucosal immune response appears important in prophylaxis or acute infection. Examples of these include respiratory viruses such as influenza or rhinovirus, poliomyelitis virus, and certain gastrointestinal viruses such as rotavirus. The vaccine of this invention may also be used against infections by viruses such as herpes virus, hepatitis B virus, human immunodeficiency virus and poxviruses, as well as other infections of mucosal like tissue including *E. coli* infection of the urinary tract and chlamydia infection of the eye in trachoma. The vaccine of the present invention can also be used to invoke a systemic immunity, suggesting uses in systemic infections such as hepatitis or tetanus. Other immunising applications such as those intended for anti-allergy or contraceptive treatment may also be appropriate.

The vaccine of this invention may comprise a plurality of antigens to produce a multivalent vaccine, for example, for a number of different strains of influenza which may be present in the population at a particular time. Alternatively or additionally, the vaccine may comprise a plurality of antigens from different organisms, thus leading to a single vaccine effective against more than one disease or condition.

The invention is not limited to the use of whole red blood cells in the vaccine, because derivatives thereof, such as ghosts or whole membrane preparations, as well as membrane fragments, can also yield the desired enhanced mucosal immunogenicity. One observation by the present inventors in work leading to the present invention has been that the use of red blood cells provides extremely uniform size particles within the optimal 5 to 10 $\mu$m range optimally taken up by Peyers patches, see, for instance Jones et al. (1988) *Scand. J. Immunol.*, 27, 645. Thus, by the use of the invention, an antigen can be effectively targeted to the Peyers patches, the "mucosal motor" for the activation of the common mucosal system. Previous attempts to target Peyers patches have failed due to difficulties in creating discrete uniform size particles, as shown by Kreuter et al. (1981) *J. Pharmaceutical Sci.* 70, 367.

An advantage of the orally administered red blood cell (or derivative)-based vaccine of the present invention is that due to previous dietary exposure, the red blood cells are immunologically well tolerated by most individuals. It is therefore desirable that the red blood cells should originate from farm animals such as chickens, ducks, cows or sheep. Alternatively, to ensure hypoallergicity human red blood cells may be used.

The surface-association of the antigen with the red blood cell or derivative may take place through adsorption or binding via liganding or other chemical modification. One form of binding which may be utilised is to bind the antigen to a lectin or antibody (or antibody fragment) having specificity for red blood cell markers. Preferably, however, the association takes place through the interaction of an indigenous (i.e. naturally present) receptor on the red blood cell, the receptor having specificity either for the antigen itself or for a linking or haptenic group attached to the antigen.

In one aspect, the present invention has particular application in vaccines where the antigen is a virus particle or viral antigen derived from a virus possessing a haemagglutinin molecule, particularly influenza virus such as type A and type B influenza virus. Preferably, the antigen comprises a virus in inactivated (or dead) or attenuated form so that it is non-infective but retains its antigenic properties. The influenza haemagglutinin glycoprotein (HA) binds avidly to a surface receptor of chicken red blood cells (CRBC). Accordingly, influenza preparations, either live attenuated or inactivated, can be directly bound via the HA and surface receptor to the red blood cell (or derivative). Virus purification from culture supernates and vaccine preparation can be achieved in a single step by the simple addition of the red blood cell (or derivative) to the culture supernate. A preferred technique for preparing viral antigens utilises the well known technique of gamma irradiation which appears to favourably maintain the antigenicity of the preparation.

The efficacy of antigen presentation on the red blood cell (or derivative) is such that very small amounts of antigen may induce an effective response, suggesting a potentiation or adjuvancy of this system. The small amounts of antigen required may allow the provision of the multivalent vaccines discussed above.

As previously described, the vaccine of this invention may comprise either the whole red blood cell, or a ghost or whole membrane preparation derived by lysis of the whole red blood cell. In addition, the vaccine may comprise membrane fragments, which may for example be derived by sonication of whole membrane preparations.

An unexpected feature of the vaccine of the present invention is that it has been shown to provide effective local and systemic stimulation, resulting in circulating and local antibodies which have a demonstrated prophylactic effect.

For oral administration, the vaccine composition of this invention may be combined with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% by weight of antigen. The percentage of the antigen in the compositions and preparations may, of course, be varied and may conveniently be between about 5 to about 80% of the weight of the unit. The effective amount of antigen in the vaccine compositions is such that a suitable dosage will be obtained to elicit the desired mucosal immune response.

Dosage units in the form of tablets, troches, pills, capsules and the like may also contain the following: a binder such as gum fragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose, or saccharin may be added or a flavouring agent such as peppermint, oil of wintergreen, or cherry flavouring. When the dosage unit form is a capsule, it may contain, in addition to materials of the above type, a liquid carrier. various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active compound may be incorporated into sustained-release preparations and formulations.

Where the vaccine is intended for animal use, the vaccine is conveniently administrable with the animal feed, such as grain, or in the animal drinking water. The vaccine composition may also be incorporated into a grain base or may be topically applied to feed grain.

As used herein carriers and/or diluents include any and all solvents, dispersion media, aqueous solutions, coatings, antibacterial and antifungal agents, isotonic and absorption delaying agents, and the like. The use of such media and agents for pharmaceutical active substances is well known in the art and is described by way of example in *Remington's Pharmaceutical Sciences,* 18th Edition, Mack Publishing Company, Pennsylvania, U.S.A. Except insofar as any conventional media or agent is incompatible with the active ingredient, use thereof in the vaccine compositions is contemplated. Supplementary active ingredients can also be incorporated into the compositions. The latter is particularly contemplated as far as the present invention extends to multivalent vaccines or multi-component vaccines.

A number of embodiments of the vaccine in accordance with the invention will now be described by way of example only, with reference to the following Examples and the accompanying FIGS. 1 to 17 which illustrate the results of the various experiments discussed in the Examples. In the accompanying Figures.

Figure 3A:
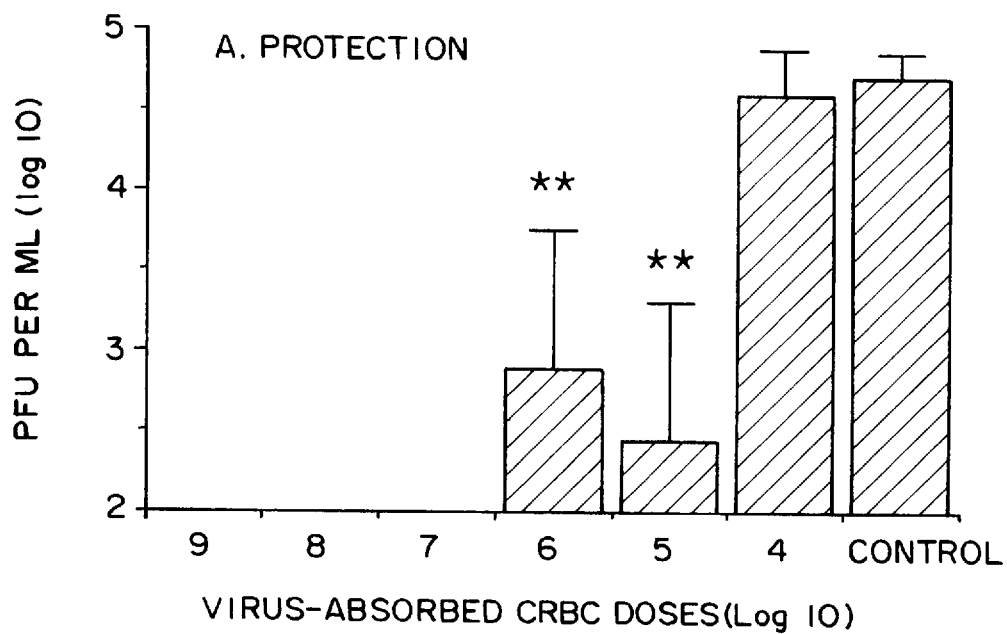
Figure 3B:
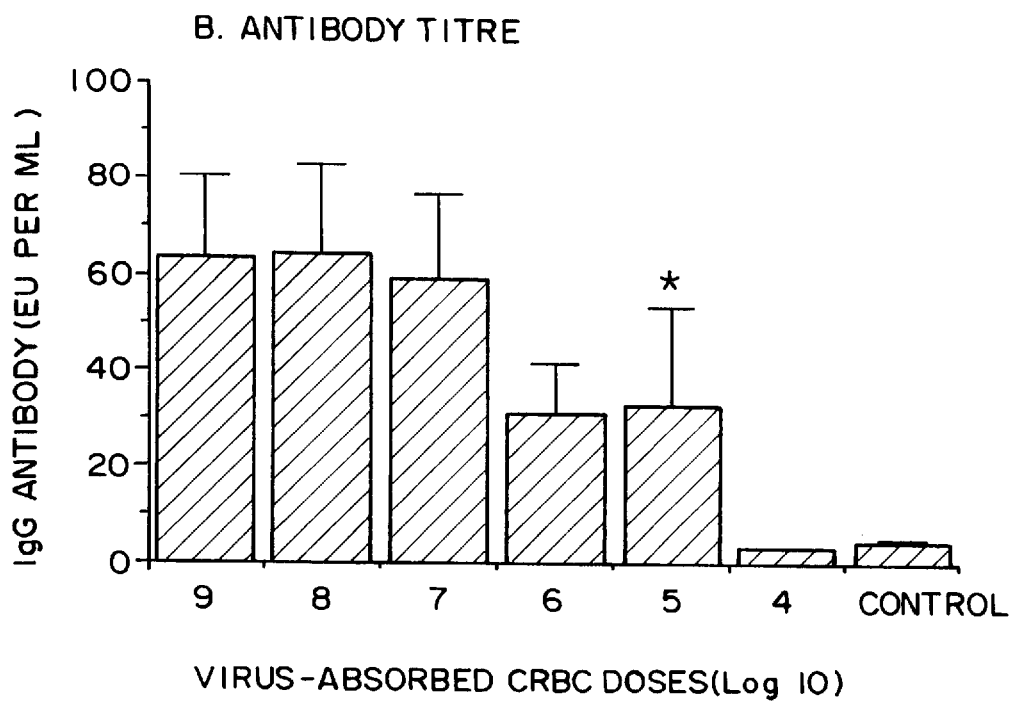
Figure 4A:
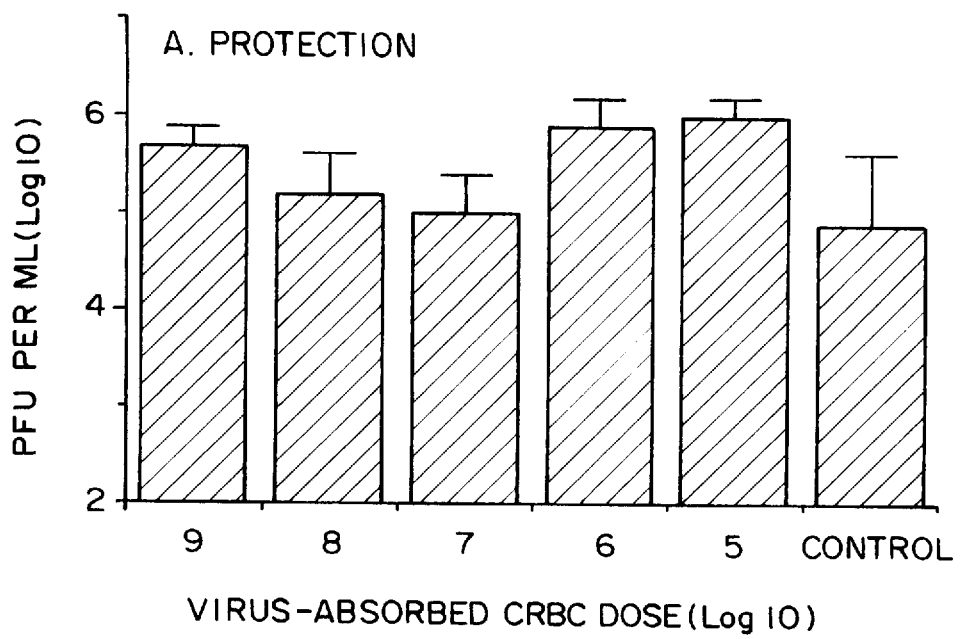
Figure 4B:
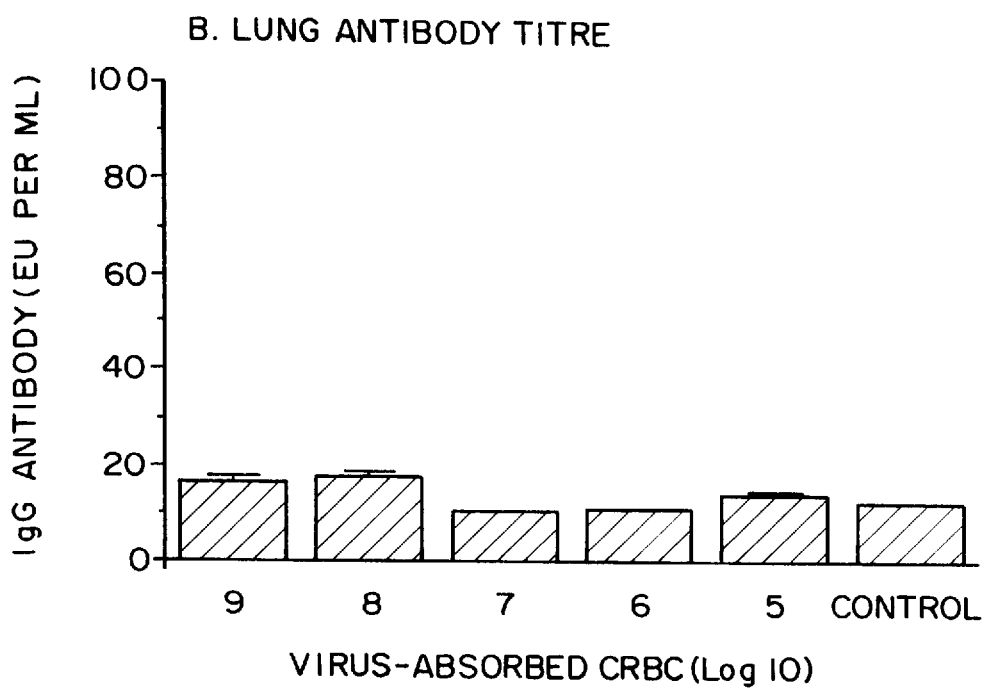
Figure 5:
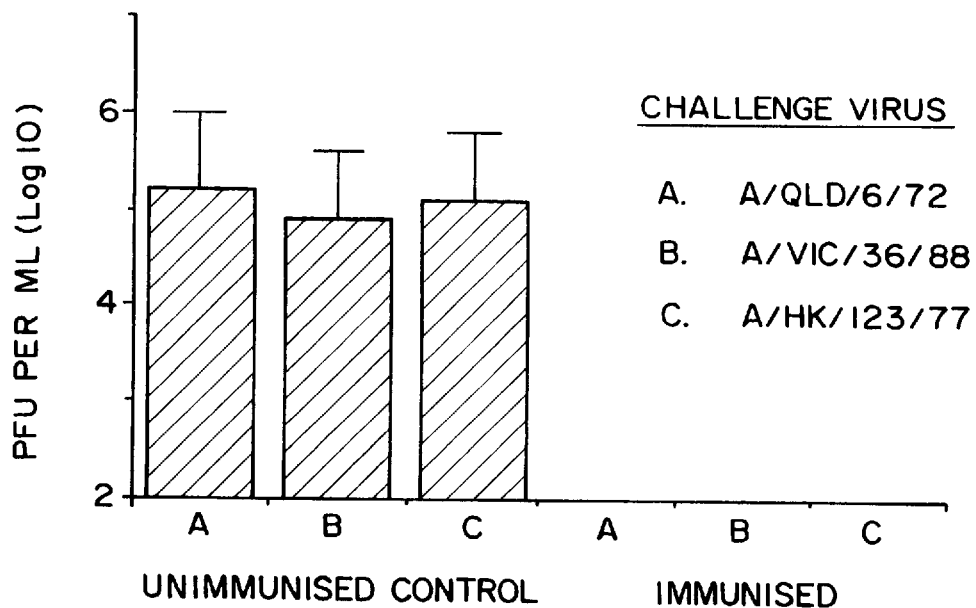
Figure 6:
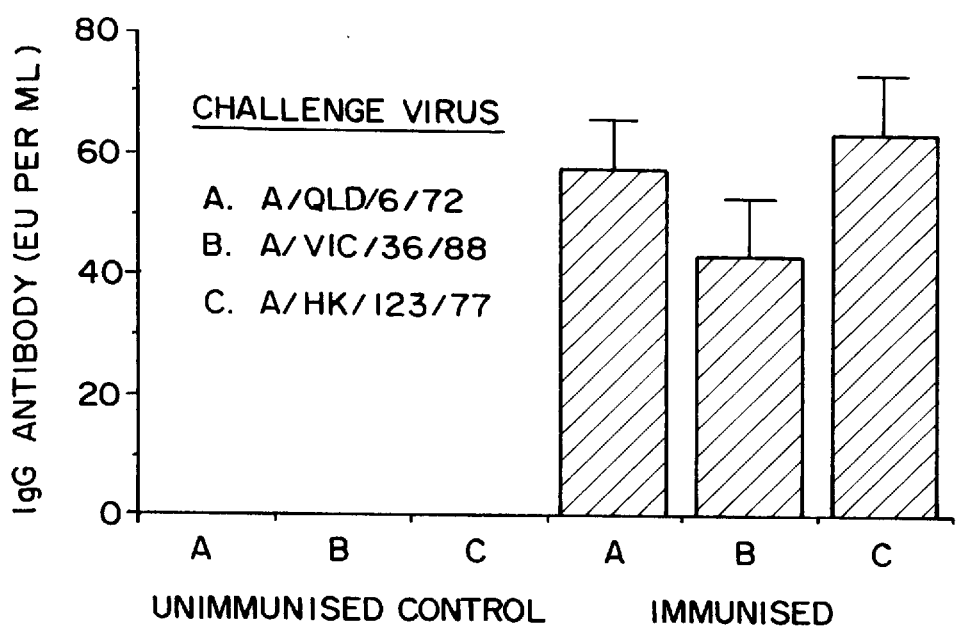
Figure 8:
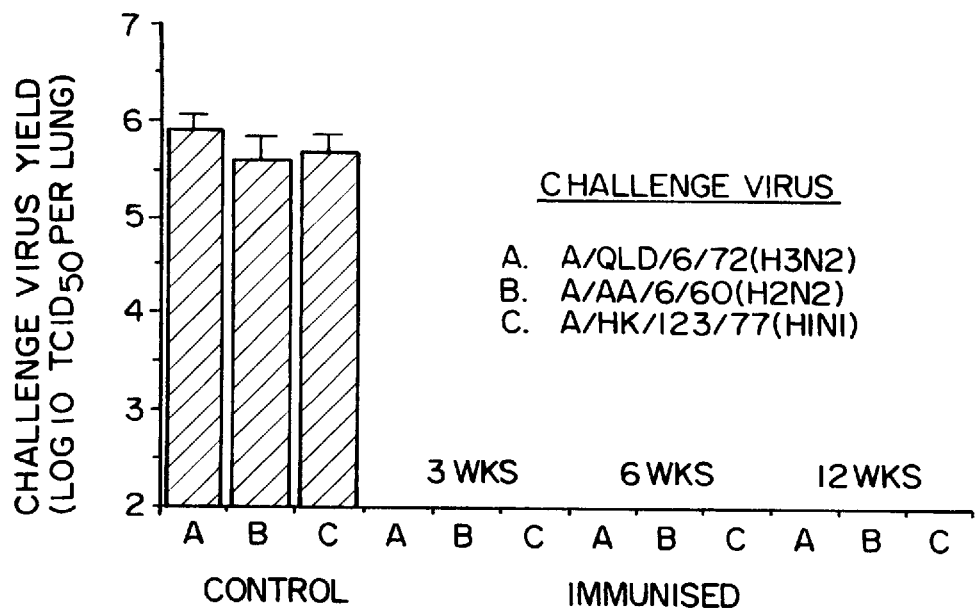
Figure 9:
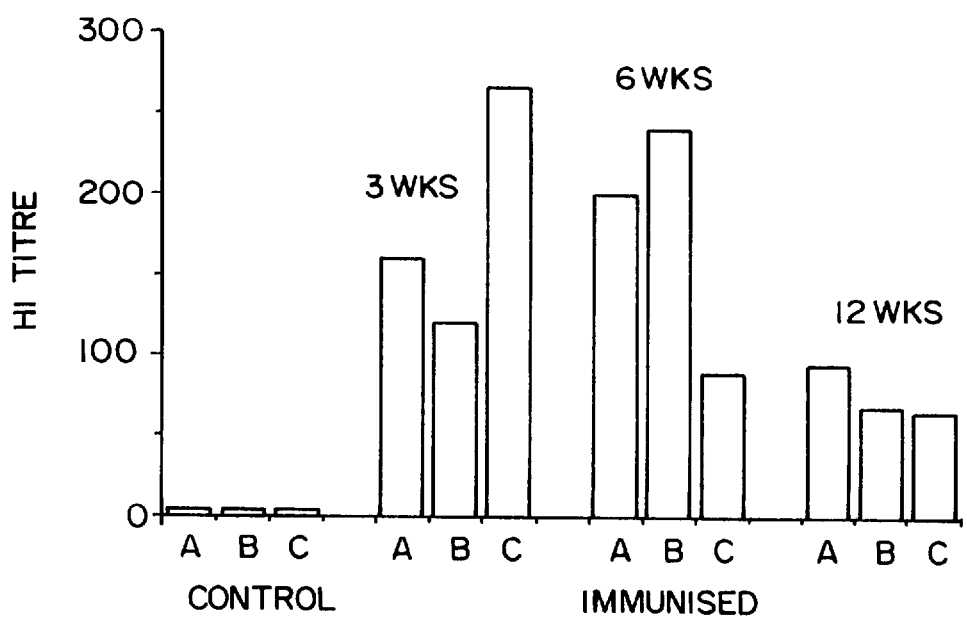
Figure 10A:
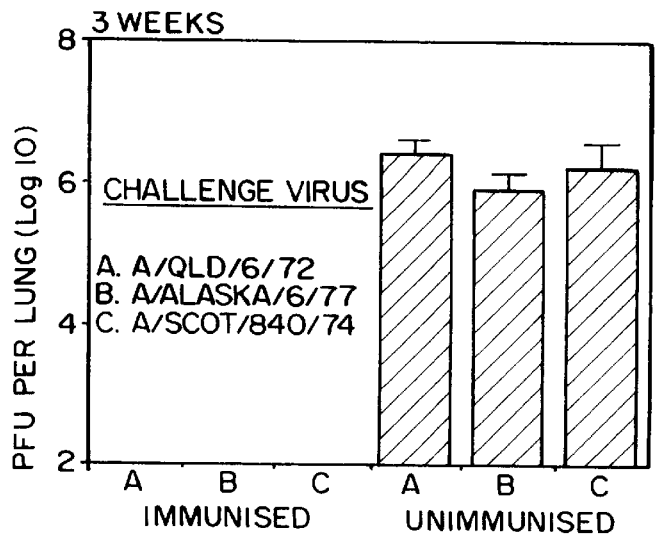
Figure 10B:
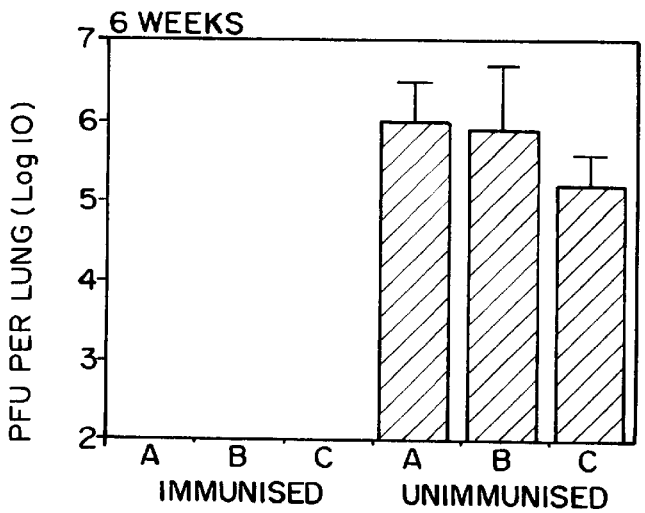
Figure 10C:
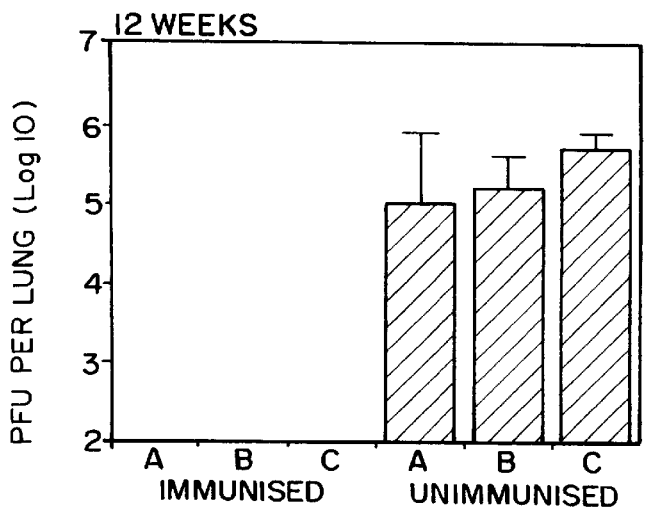
Figure 11A:
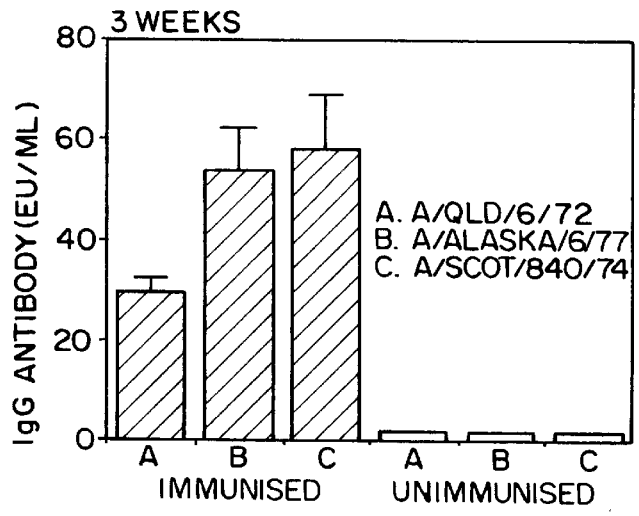
Figure 11B:
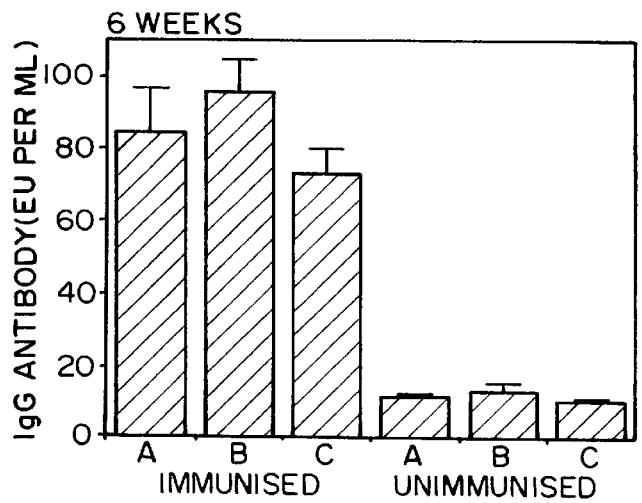
Figure 11C:
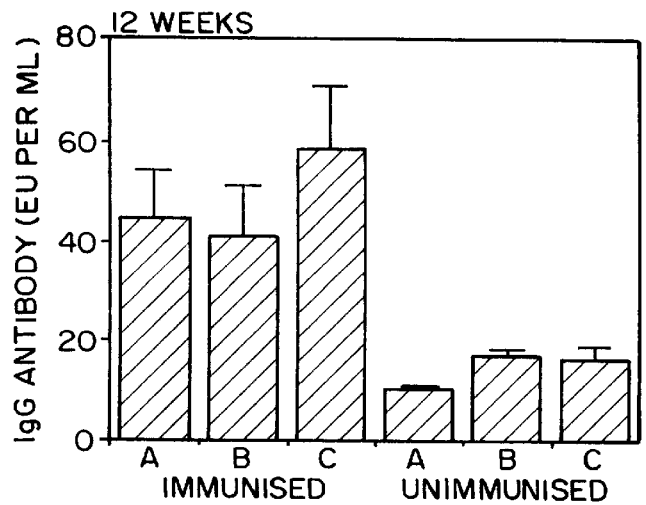
Figure 12:
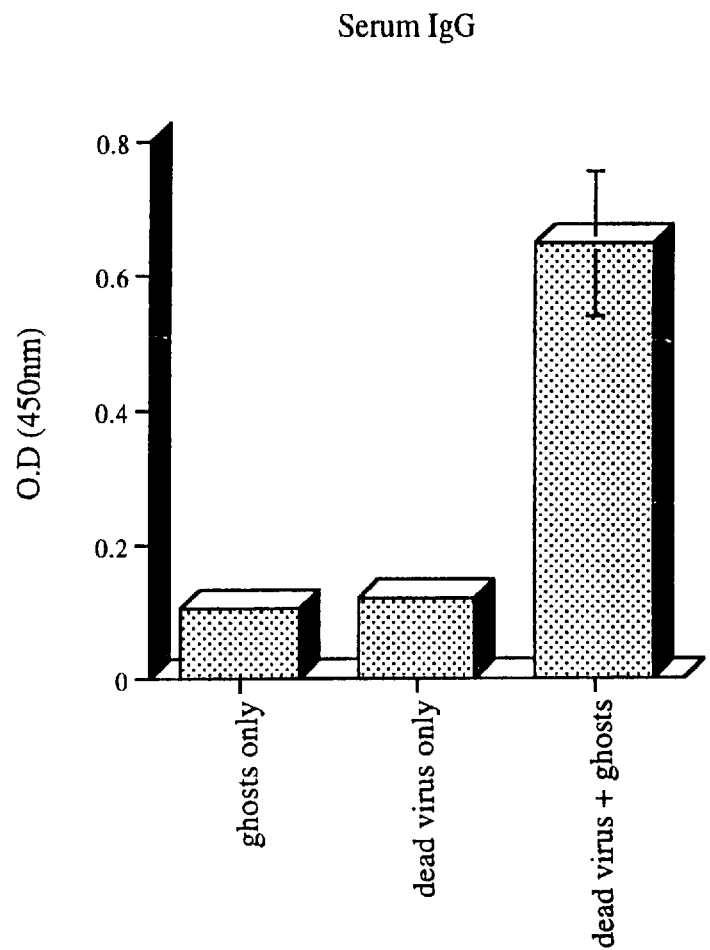
Figure 13:
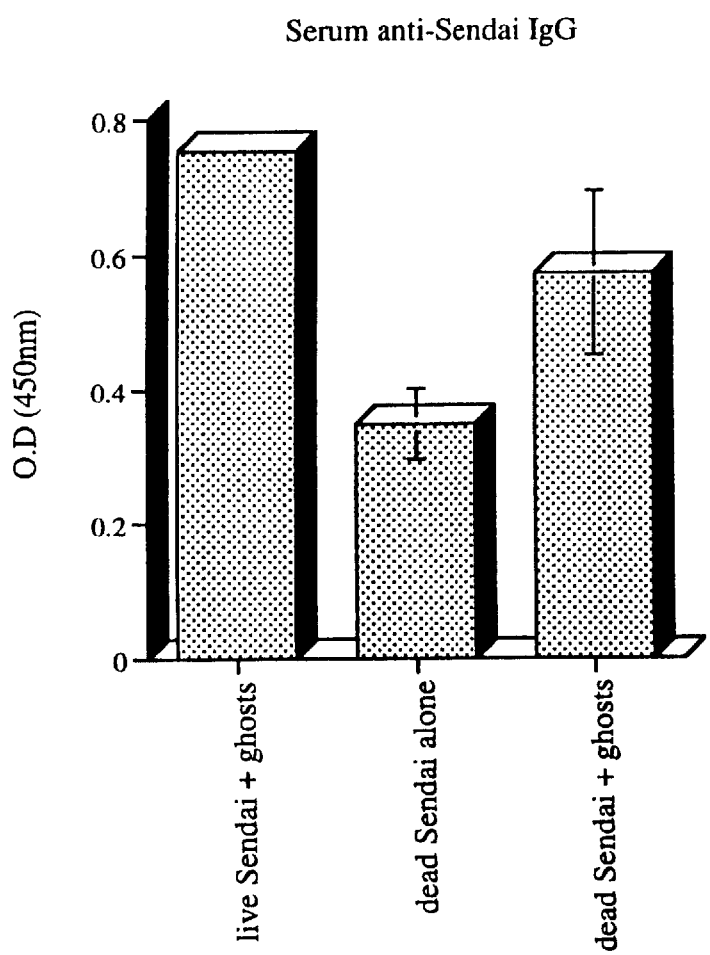
Figure 14:
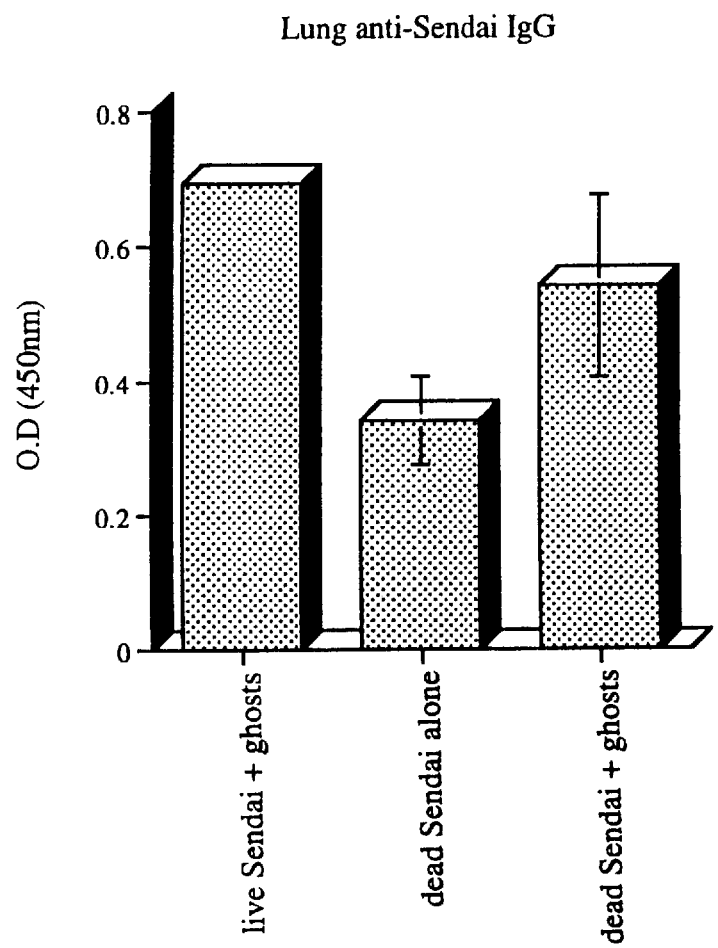
Figure 15:
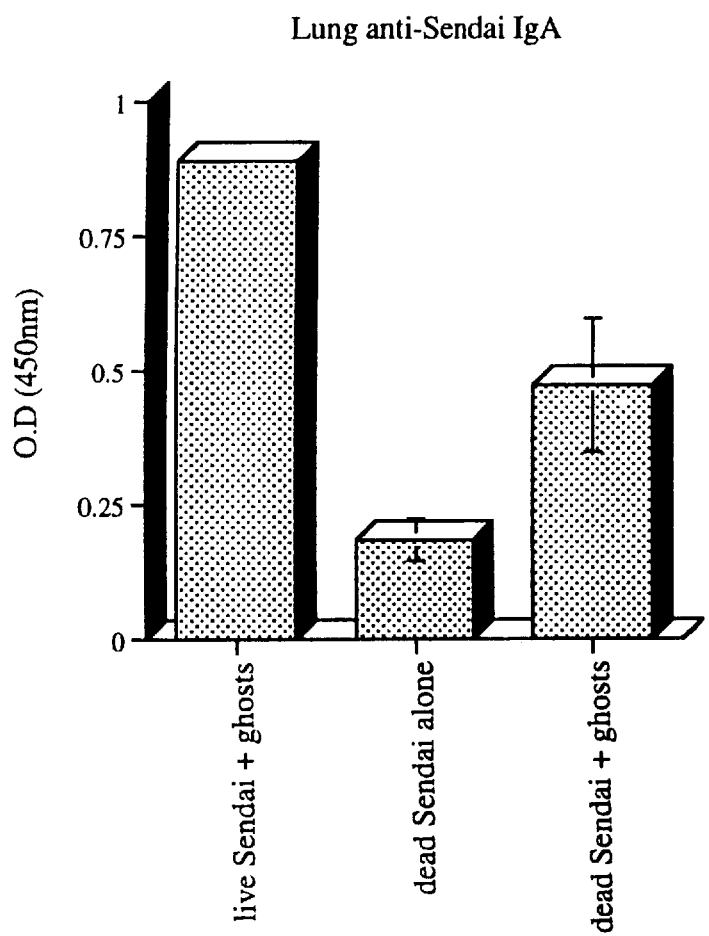
Figure 16:
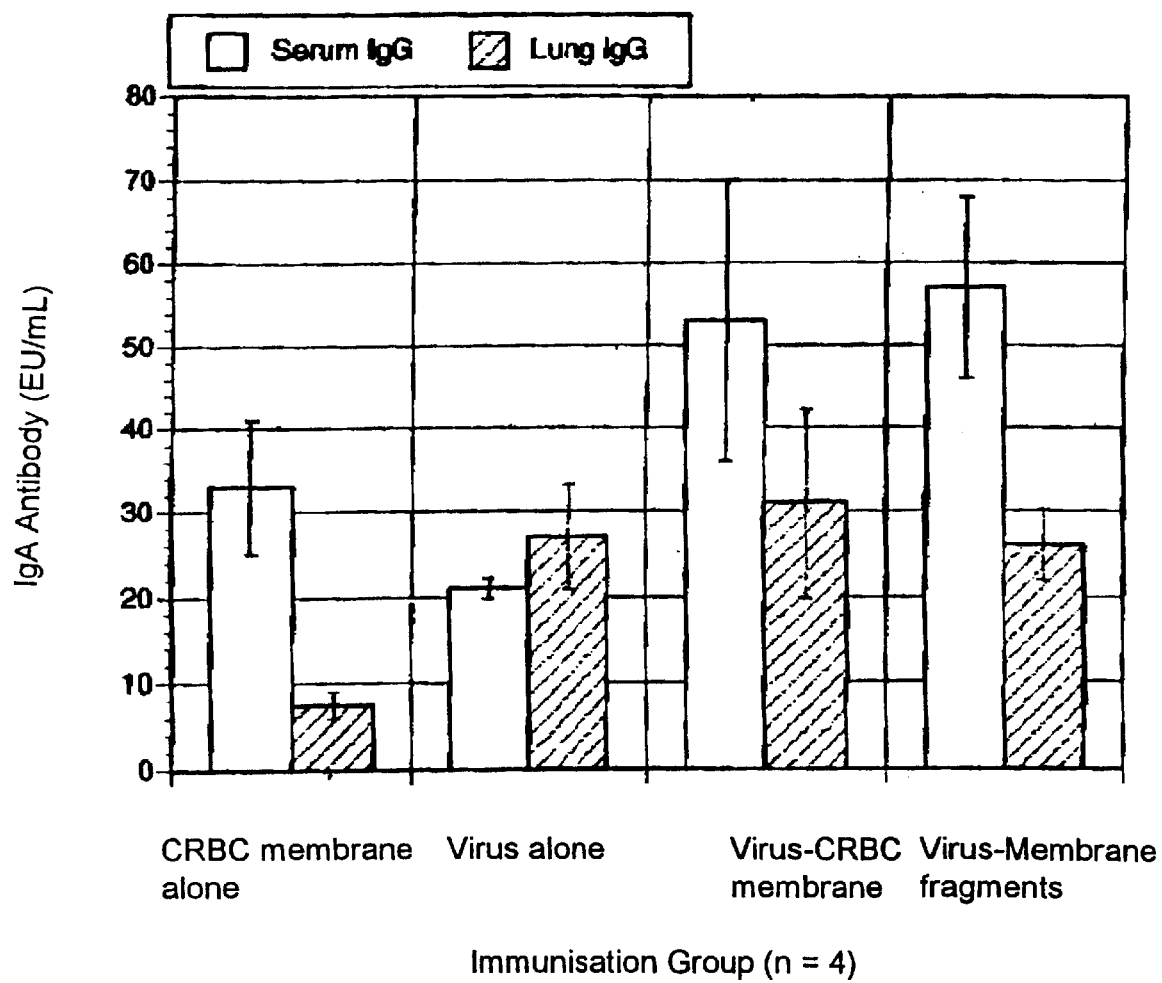
Figure 17:
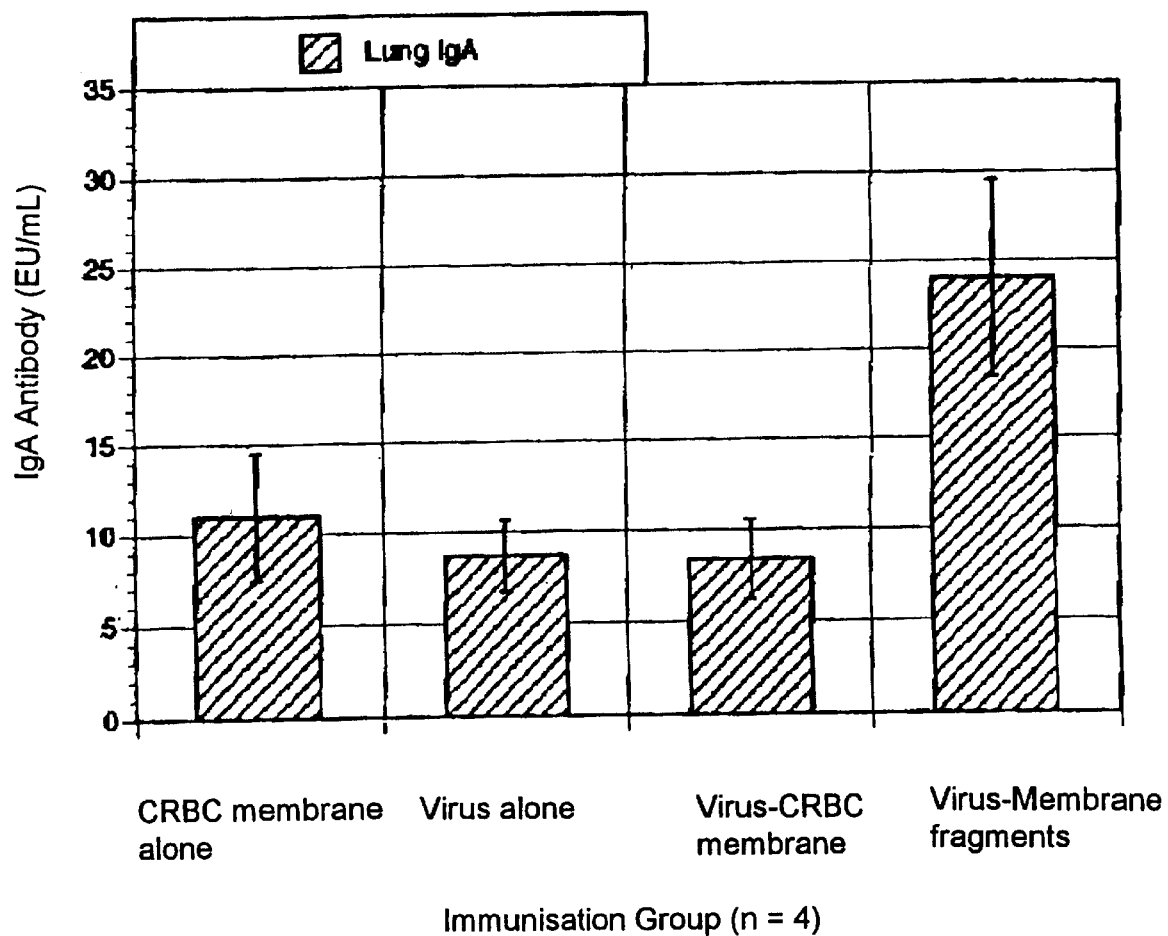

FIGS. 3 A–B are bar graphs depicting lung antibody titre and protection of mice following oral vaccination with graded doses of CRBC adsorbed with A/Qld/6/72 virus:

FIGS. 4 A–B are bar graphs depicting a similar experiment to FIG. 3 except the mice were immunised subcutaneously;

FIG. 5 is a bar graph depicting the protection of mice to A/Qld/6/72, A/Vic/36/88 and A/HK/123/77 viruses following oral immunisation with triple adsorbed virus;

FIG. 6 is a bar graph depicting virus antibody specific for A/Qld/6/77, A/Vic/36/88 and A/HK/123/77 viruses following oral immunisation with triple adsorbed virus;

FIG. 7 is a bar graph of a comparative experiment depicting cross protection of mice to H2N2 and H1N1viruses after oral vaccination with live H3N3 viruses (A/Qld/6/72);

FIG. 8 is a bar graph depicting cross protection against heterotypic challenge in mice 3, 6 and 12 weeks after oral administration with A/Qld/6/72 (H3N3);

FIG. 9 is a bar graph depicting haemagglutination inhibition titre in lung homogenates of mice following oral immunisation with CRBC adsorbed with A/Qld/6/72 (H3N3) virus;

FIG. 10 is a bar graph depicting homotypic cross protection induced by A/Qld/6/72 (H3N2) to differing viruses within the H3N2 subtype at 3,6 and 12 weeks;

FIG. 11 is a bar graph depicting correlation between antibody titre and homotypic cross protection over time at 3,6 and 12 weeks;

FIG. 12 is a bar graph showing the efficacy of a chicken red blood cell ghost preparation as a carrier for dead A/Qld/6/72 influenza virus;

FIGS. 13, 14 and 15 are bar graphs showing the efficacy of a chicken red blood cell ghost preparation as a carrier for Sendai virus in increasing serum IgG, lung IgG and lung IgA levels, respectively; and FIGS. 16 and 17 are bar graphs showing the efficacy of red blood cell whole membrane and membrane fragment preparations as carriers for A/Beijing (H3N2) influenza virus.

EXAMPLE 1

Oral Immunisation with Inactivated Influenza Viruses using Chicken Red Particles as Carriers.

This Example is based on the ability of influenza virus, irrespective of antigenic drift, to bind to chicken red blood cell surface receptor through the haemagglutinin glycoprotein. Thus virus purification and vaccine preparation can be achieved in one single step. Briefly, chicken red blood cells were washed three times with phosphate-buffered saline (PBS) and then resuspended to $10^{10}$ cells/ml in PBS. They were then used whole for virus adsorption or as 'ghosts' after lysis with Tris-buffered ammonium chloride solution. Adsorption was carried out at room temperature for 30 minutes with various dilutions of gamma irradiated ($2 \times 10^6$ rads, $^{60}$Co) allantoic fluid containing virus grown in specific pathogen free eggs. After three washes with PBS to remove egg material and excess virus, virus-adsorbed CRBC were then resuspended in 2% sodium bicarbonate solution to $5 \times 10^8$ particles/ml.

For oral vaccination, Swiss male mice were administered with 0.4 ml phosphate-buffered (unimmunised control) or 0.4 ml inactivated virus alone or CRBC (whole or lysed) absorbed with gamma irradiated virus (immunised) in sodium bicarbonate on each of days 1, 3 and 5. Ten days after the final dose the mice were challenged with live virus intranasally by inoculating 50 μl of live virus suspension in phosphate-buffered saline into each nostril using a micro pipette. Four days after challenge, mice were killed. Virus and antibody titres in the lung homogenates were determined by MCDK virus infectivity assay and ELISA.

Figure 1:
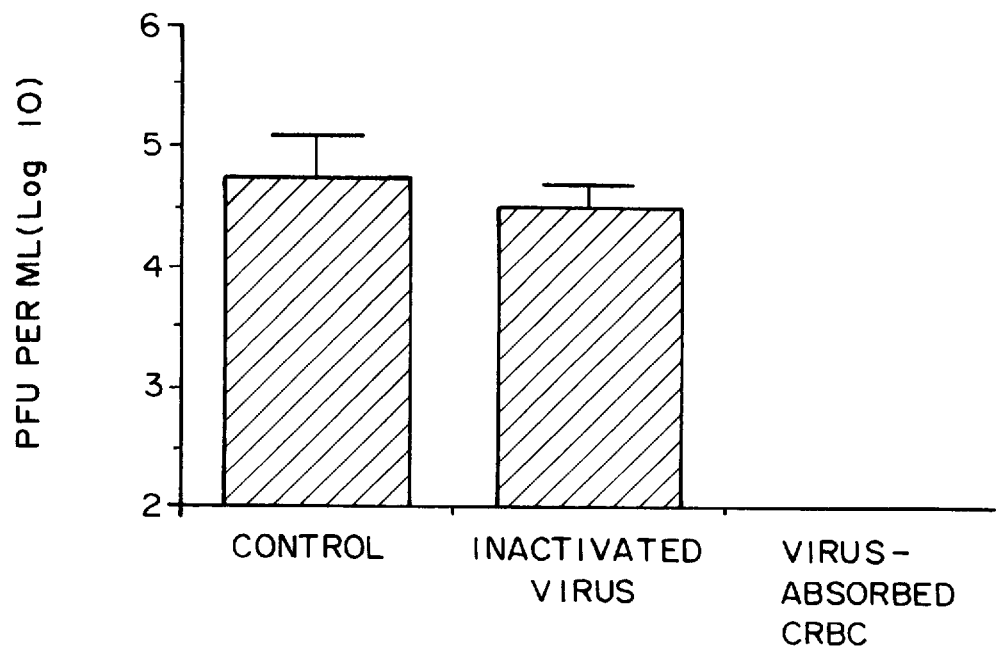
FIG. 1 is a bar graph depicting the protection of mice to H3N2 viruses after oral vaccination with CRBC adsorbed with A/Qld/6/72 virus.
Figure 2:
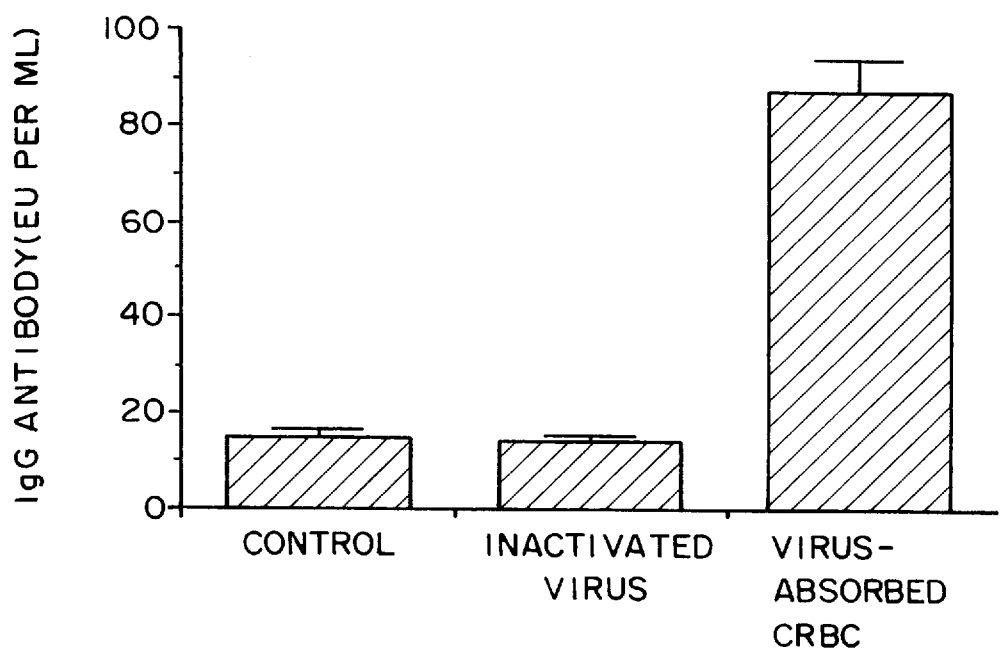
FIG. 2 is a bar graph depicting virus specific antibody titres of lung homogenates from mice after oral vaccination with virus adsorbed CRBC.

A representative experiment is shown in FIGS. 1 and 2. Mice immunised with PBS or inactivated virus were not protected against challenge with live virus in the respiratory tract compared to mice immunised with CRBC adsorbed with gamma irradiated viruses. Further, there was a correlation between protection and the presence of virus-specific antibodies in respiratory secretion (FIG. 2). Protection and antibody response were dose-dependent, with mice being protected when immunised with CRBC adsorbed with virus as low as $\log_{10}$ 2 TCID as depicted in Table 1 which shows the antibody response and protection of mice from lung infection following oral vaccination with graded doses of A/Qld/6/72 virus adsorbed to CRBC.

TABLE 1

Antibody response and protection of mice from lung infection following oral immunisation with CRBC absorbed with graded doses of inactivated A/Qld/6/72 (H3N2) virus.

| A/Qld/6/72 (H3N2) Immunization Dose | Lung | | Nasal Wash | |
|---|---|---|---|---|
| ($\log_{10}$ TCID$_{50}$) | IgG (Eu/ml) | PFU/Lung | IgA (EU/MI) | PFU/ml |
| 0 | 4.8 ± 0.002 | 6.06 ± 0.08 | 5.6 ± 0.09 | 4.6 ± 0.15 |
| <1 | 17.2 ± 0.79 | 5.40 ± 0.24 | 10.1 ± 0.59 | 4.4 ± 0.23 |
| 2 | 67.5 ± 11.3 | 2.67 ± 0.84 | 51.6 ± 0.13 | <2 |
| 3 | 65.9 ± 8.5 | <2 | 42.9 ± 14.3 | <2 |
| 4 | 65.4 ± 8.4 | <2 | 14.9 ± 0.50 | <2 |

By comparing FIGS. 3 and 4 it can be seen that lung antibody titre following oral vaccination with the product of this invention is enhanced over that seen from subcutaneous administration. The versatility of the CRBC carrier system was demonstrated in an experiment in which triple absorbed virus CRBC was tested using A/Qld/6/72, A/Vic/36/88, and A/HK/123/77 viruses. All three viruses were cleared from the murine lung following challenge and the responses correlated with virus-specific antibody levels in respiratory secretion (FIGS. 5 and 6). Clearly, virus-absorbed CRBC particles are potent inducers of protective immunity in the respiratory tract when administered by the oral route. Table 2 includes preliminary data from current studies, indicating cross protection following oral immunisation with absorbed virus.

TABLE 2

Cross specific virus antibody* in respiratory secretion of mice following oral immunisation with A/6/Qld2/72 (H3N2) influenza virus absorbed to CRBC.

| | A/Vic/36/68 (H1N1) | A/HK/123/77 (H1N1) | A/Qld/2/72 (H3N2) | *V(GT)007 (H6N1) (Recombinant) | *V(GT)-035/79 (H2N2) (Wild variant) | *B/Vic/2/87) |
|---|---|---|---|---|---|---|
| Unimmunised | — | — | 4.6 ± 0.008 | — | — | |
| Immunised- A/Qld/6/72 (H3N2) absorbed CRBC | 68.4 ± 8.5 | 78.5 ± 9 | 123 ± 20 | 86.3 ± 9.0 | 95.4 ± 9.5 | 7.6 ± 0.7 |

*ELISA assay including whole virus.

Heterotypic cross protection and the duration of protection were assessed by immunising groups of mice with $4 \times 10^7$ A/Qld/6/72 (H3N2) virus absorbed CRBC and challenging each group with $\log_{10}$ 5.6 TCID A/Qld/6/72 (H3N2), A/AA/6/60ca (H1N1) and A/HK/123/77 (H2N2) respectively. Three weeks, 6 weeks and 12 weeks after oral immunisation, mice were challenged with live wildtype viruses from different subtypes. As shown in FIG. 8, viruses were completely cleared from the lung. Virus clearance correlated with antibody against the homologous strain as well as cross protective antibody against the heterologous strains. Similar results were observed in the nasal wash in terms of virus clearance and antibody levels. The results were validated using the H1 test to determine antibody levels in lung homogenates and nasal washes, which correlate with protection.

Homotypic cross protection induced by A/Qld/6/72 H3N2 to differing viruses within the H3N2 subtype is depicted In FIG. 10 while FIG. 11 correlates antibody titre and homotypic cross protection in this system.

A remarkable level of cross protection (across the haemagglutinin barrier) was demonstrated using ELISA antibody assay. This cross protection could be directly demonstrated using in vivo challenge. This protection (antibody production and pulmonary clearance) could be demonstrated to remain relatively undiminished for at least three months following a primary immunisation. Antigen specificity was further examined using haemagglutination inhibition titres, and again, cross protection was demonstrated, indicating an extraordinary production of haemagglutinin specific antibodies (FIG. 9), although by 12 weeks antibody titres were falling.

Thus it would appear that immunisation with a vaccine in accordance with the invention stimulates a broad immunity that crosses the "haemagglutinin barrier" of systemic immunisation using a very small amount of virus. By way of example, FIG. 7 indicates that cross protection is not seen in orally administered influenza vaccine in the absence of the red blood cells (or derivatives).

EXAMPLE 2

The following experiment clearly demonstrates the efficacy of a red blood cell ghost preparation as an antigen carrier. The results are shown in FIG. 12. The Figure shows serum IgG responses of mice vaccinated orally with chicken red blood cell ghosts alone, dead (30 k Gy-irradiated) influenza virus alone and dead influenza associated with chicken red blood cell ghosts in accordance with the present invention. The influenza virus used was strain A/Queensland/6/72.

Control mice orally vaccinated with either chicken red blood cells alone or dead virus alone displayed significantly lower serum IgG levels when compared to mice vaccinated with the dead virus/chicken red blood cell ghost preparation.

EXAMPLE 3

In order to demonstrate the efficacy of red blood cells as antigen carrier for other viruses possessing a haemagglutinin molecule, the experiment of Example 2 was repeated using Sendai virus coupled to chicken red blood cell ghosts.

FIGS. 13, 14 and 15 show, respectively serum IgG, lung IgG and lung IgA responses of mice vaccinated orally with live Sendai virus associated with chicken red blood cell ghosts, dead Sendai virus alone and dead Sendai virus associated with chicken red blood cell ghosts.

Control mice orally vaccinated with dead virus alone displayed significantly lower serum IgG, lung IgG and lung IgA levels when compared to mice vaccinated with either the live virus/chicken red blood cell ghost preparation or the dead virus/chicken red blood cell ghost preparation.

EXAMPLE 4

This example relates to compositions comprising whole membranes and membrane fragments of chicken red blood cells (CRBC) adsorbed with inactivated influenza viruses which would normally be less immunogenic, and to their use as oral vaccines against influenza virus infection. The oral vaccine comprising virus adsorbed to membrane fragments (as opposed to whole cell membrane) is particularly capable of eliciting an immune response in terms of a secretory IgA antibody response in the lung.

The method and results obtained are as follows:

(i) Whole CRBC membranes were prepared by lysing CRBC in 0.05% acetic acid in sterile distilled water. After washing in PBS, the membranes were counted and adjusted to $10^8$ cells/mL.

(ii) The CRBC membranes were adsorbed with irradiated A/Beijing (H3N2) influenza virus at $10^8$ PFU/mL at 4° for 1 hr. After centrifugation at 200 g, the virus-CRBC complexes were washed twice in PBS and resuspended at $10^8$ particles per mL in 2% sodium bicarbonate containing 1% gelatin.

(iii) The CRBC-virus preparation was cooled on ice and then sonicated 3 times for 15 secs with a cooling period of 5 sec interval with an amplitude setting at 10 using a MSE Soniprep. The sonicated preparations were monitored for disrupted membrane fragments by light microscopy.

(iv) The CRBC-virus membrane fragments were used to immunise Swiss outbred mice, each given 0.4 mL ($4 \times 10^7$ particles per mouse, n=4) by intragastric route on days 1, 3, 5, 12 and 19. Controls include CRBC membrane alone, irradiated A/Beijing virus alone, and irradiated A/Beijing virus adsorbed to whole CRBC membrane.

v) Mice were challenged on day 22. After 3 days, serum and lung homogenates were tested for IgG and IgA antibody.

(vi) The results shown in FIGS. 16 and 17 demonstrate that comparable IgG virus antibody levels were detected in both serum and lung homogenate in mice following oral immunisation with whole or fragmented membrane adsorbed with A/Beijing influenza virus. In contrast, a predominantly IgA antibody response was detected in the lungs of mice immunised with membrane fragments adsorbed with virus.

What is claimed is:

1. An oral vaccine comprising an antigen derived from a virus possessing a haemagglutinin molecule, wherein said antigen is surface associated with a red blood cell, a ghost preparation thereof or a whole membrane preparation or fragments thereof, and wherein said vaccine elicits a mucosal immune response in mammals.

2. A vaccine according to claim 1 wherein the antigen is protein.

3. A vaccine according to claim 1 wherein said viral antigen is a virus particle.

4. The vaccine according to claim 1 wherein said viral antigen comprises an influenza virus particle.

5. A vaccine according to claim 1, 3 or 4, wherein the viral antigen comprises live attenuated virus.

6. A vaccine according to claim 1, 3 or 4, wherein the viral antigen comprises inactivated virus.

7. A vaccine according to claim 1 wherein the viral antigen is an influenza antigen.

8. A vaccine according to claim 7 wherein the influenza antigen comprises influenza virus inactivated by gamma irradiation.

9. A vaccine according to claim 1 wherein the antigen is absorbed to the surface of the red blood cell, ghost preparation, or whole cell membrane preparation or fragments thereof.

10. A vaccine according to claim 1 wherein the antigen is chemically coupled to the red blood cell, ghost preparation, or whole cell membrane preparation or fragments thereof.

11. A vaccine according to claim 1 wherein the antigen binds an indigenous surface receptor of the red blood cell, ghost preparation, or whole cell membrane preparation or fragments thereof.

12. A vaccine according to claim 1 wherein the antigen is surface-associated with a chicken red blood cell, ghost preparation, or whole cell membrane preparation or fragments thereof.

13. A vaccine to claim 1 wherein the antigen is surface-associated with a duck red blood cell, ghost preparation, or whole cell membrane preparation or fragments thereof.

14. A vaccine according in claim 1 wherein the antigen is surface-associated with a cow red blood cell, ghost preparation, or whole cell membrane preparation or fragments thereof.

15. A vaccine according to claim 1 wherein the antigen is surface-associated with a sheep red blood cell, ghost preparation, or whole cell membrane preparation or fragments thereof.

16. A vaccine according to claim 1 wherein the antigen is surface-associated with a human red blood cell, ghost preparation, or whole cell membrane preparation or fragments thereof.

17. A multivalent oral vaccine comprising a plurality of antigens, wherein at least one antigen of said plurality of antigens is an antigen derived from a virus possessing a haemagglutinin molecule, and wherein said antigen is surface-associated with a red blood cell, a ghost preparation thereof, or a whole cell membrane preparation or fragments thereof, and wherein said vaccine elicits a mucosal immune response in mammals.

18. A method for eliciting a mucosal immune response in a mammal, said method comprising orally administering to said mammal a vaccine as claimed in claim 1 in an amount effective to elicit said mucosal immune response.

19. A method according to claim 18, wherein the mammal is a human.

20. A method for inducing a systemic immune response in a mammal, said method comprising orally administering to said mammal a vaccine according to claim 1 in an amount effective to induce said systemic immune response.

21. The method according to claim 20, wherein said mammal is a human.

* * * * *